United States Patent [19]

Christensen et al.

[11] Patent Number: 4,487,602
[45] Date of Patent: Dec. 11, 1984

[54] INJECTION DEVICE

[75] Inventors: Terrence B. Christensen; Allen D. McNaughton, both of Mountain View; Steven R. Umbach, Menlo Park, all of Calif.

[73] Assignee: Syntex (U.S.A.) Inc., Palo Alto, Calif.

[21] Appl. No.: 531,871

[22] Filed: Sep. 13, 1983

Related U.S. Application Data

[63] Continuation of Ser. No. 301,661, Sep. 14, 1981, Pat. No. 4,403,989.

[51] Int. Cl.³ .............................................. A61M 5/00
[52] U.S. Cl. ................................................... 604/137
[58] Field of Search ............... 604/137, 134, 135, 136, 604/150, 151, 156, 157, 162

[56] References Cited

U.S. PATENT DOCUMENTS

| | | | |
|---|---|---|---|
| 3,964,481 | 6/1976 | Gourlandt et al. | 604/137 |
| 4,108,176 | 8/1978 | Walden | 604/137 |
| 4,177,810 | 12/1979 | Gourlandt | 604/137 |
| 4,276,879 | 7/1981 | Yiournas | 604/137 |

Primary Examiner—John D. Yasko
Attorney, Agent, or Firm—John A. Dhuey

[57] ABSTRACT

An injection device particularly suitable for the intraruminal injection of ruminants is described. The injection device is characterized by a needle carrying means and a needle actuation means, which are operatively coupled such that the needle actuation means permits movement of the needle carrying means from a retracted position to an extended position, wherein the needle is capable of piercing the rumen, only when the needle carrying means is in a preferred orientation (e.g. perpendicular) to the surface of the host animal at the injection site. The injection device is further characterized by a dose delivery actuation means which is responsive to the relative position of the needle carrying means and the needle actuation means such that the dose is delivered to the host animal only when the needle carrying means and the needle actuation means are in a preferred position relative to each other. The characteristic features of the described injection device substantially prevent the application of a dose to a host animal not within an intended dose delivery area.

3 Claims, 11 Drawing Figures

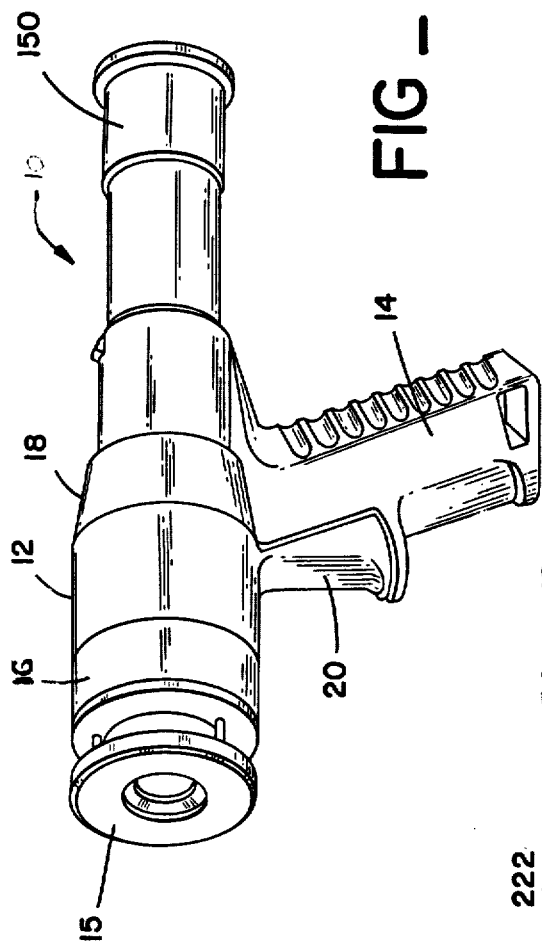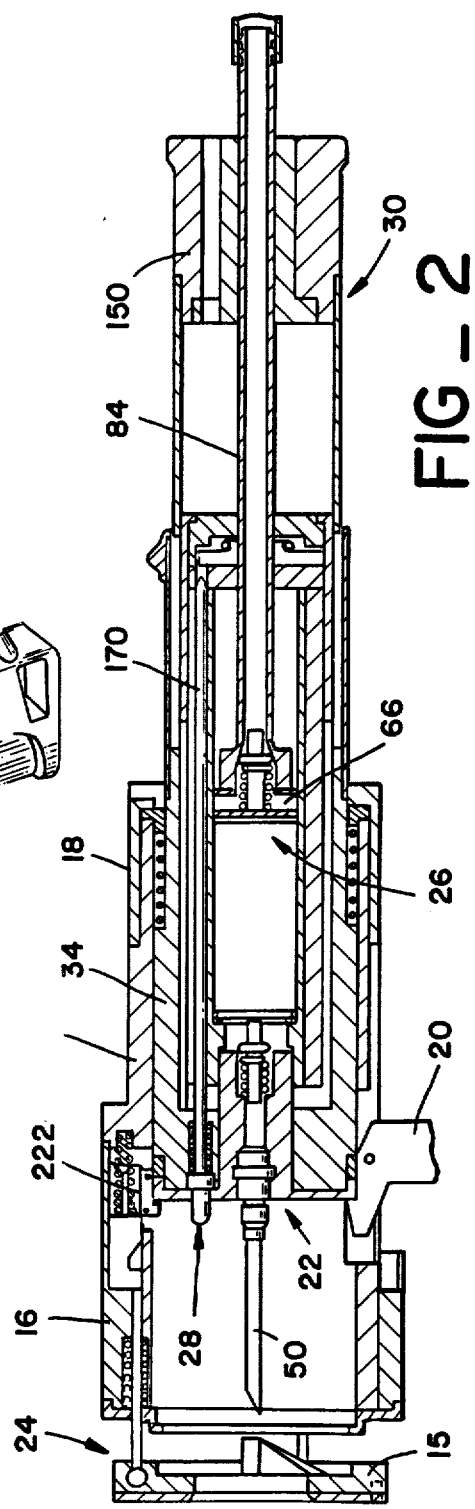

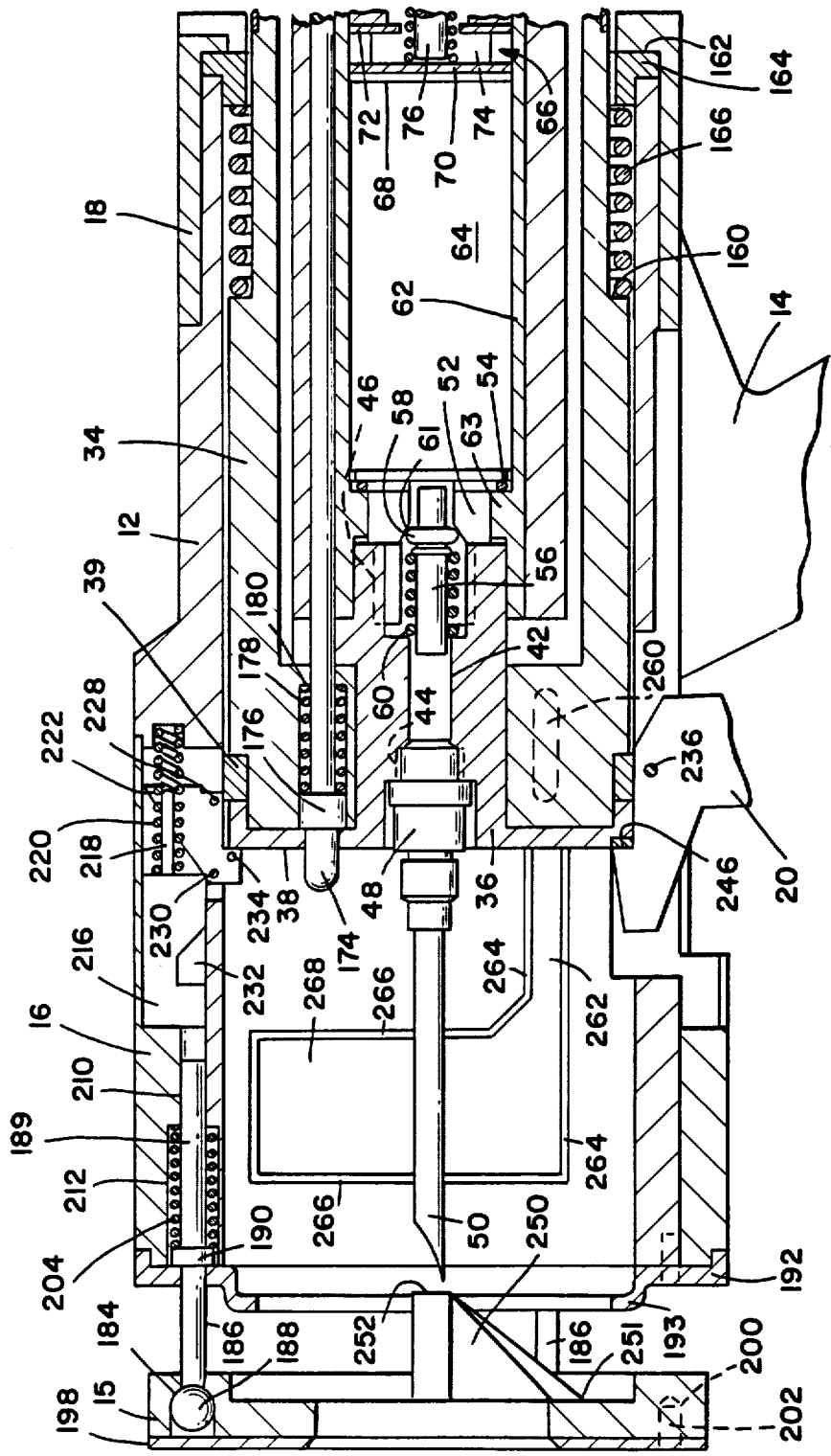
FIG_2A

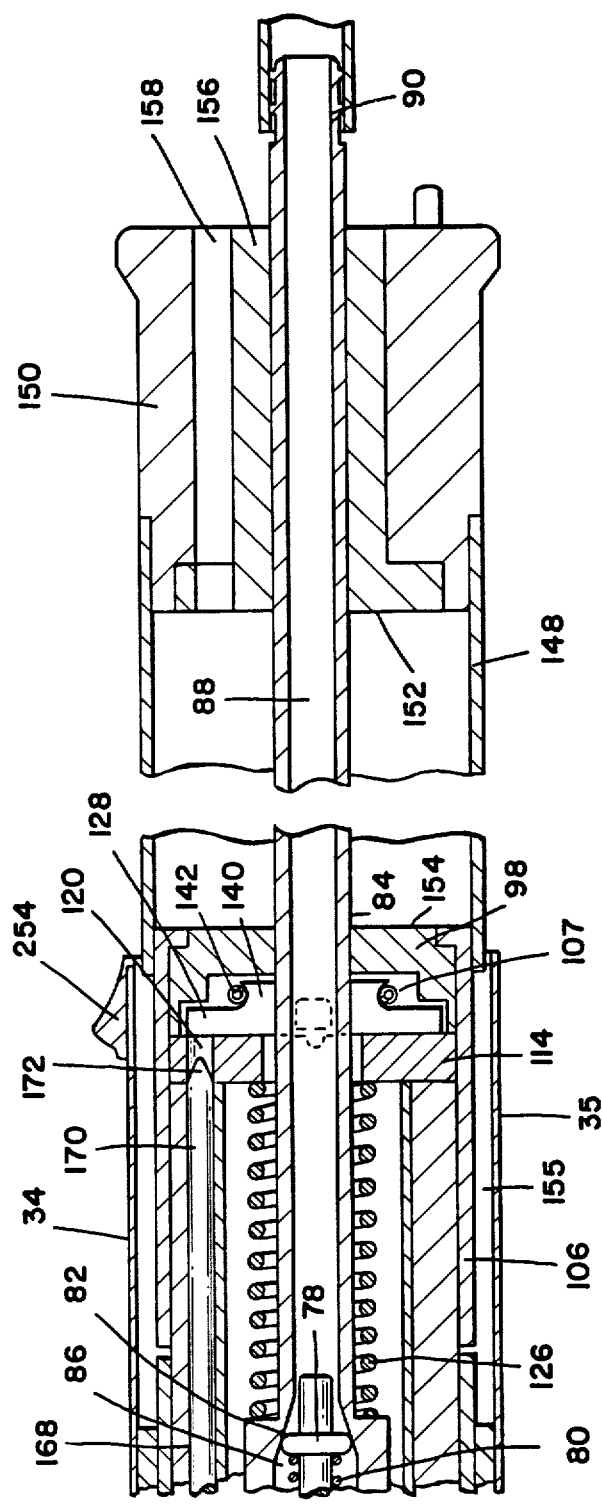
FIG_2B

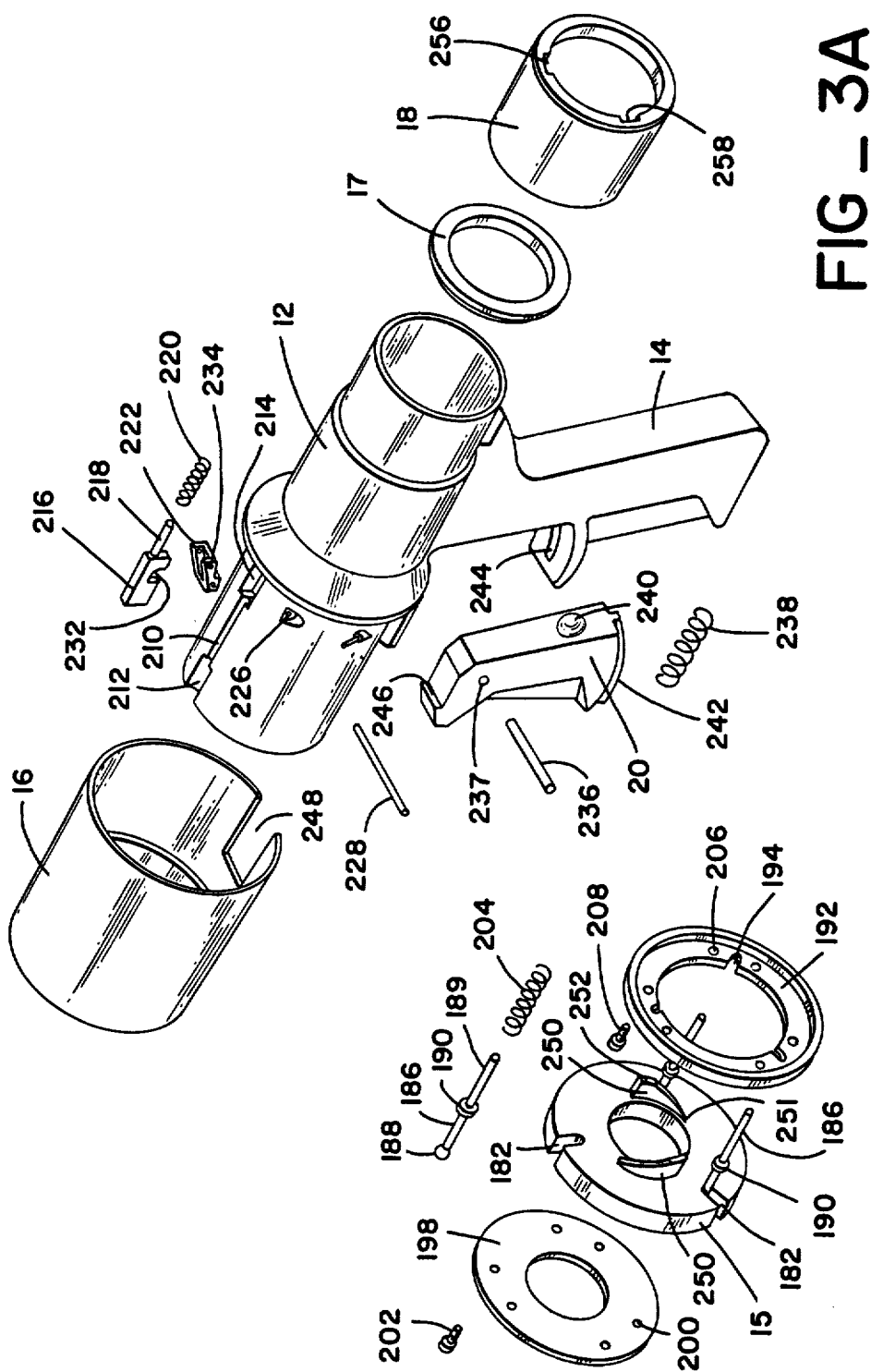

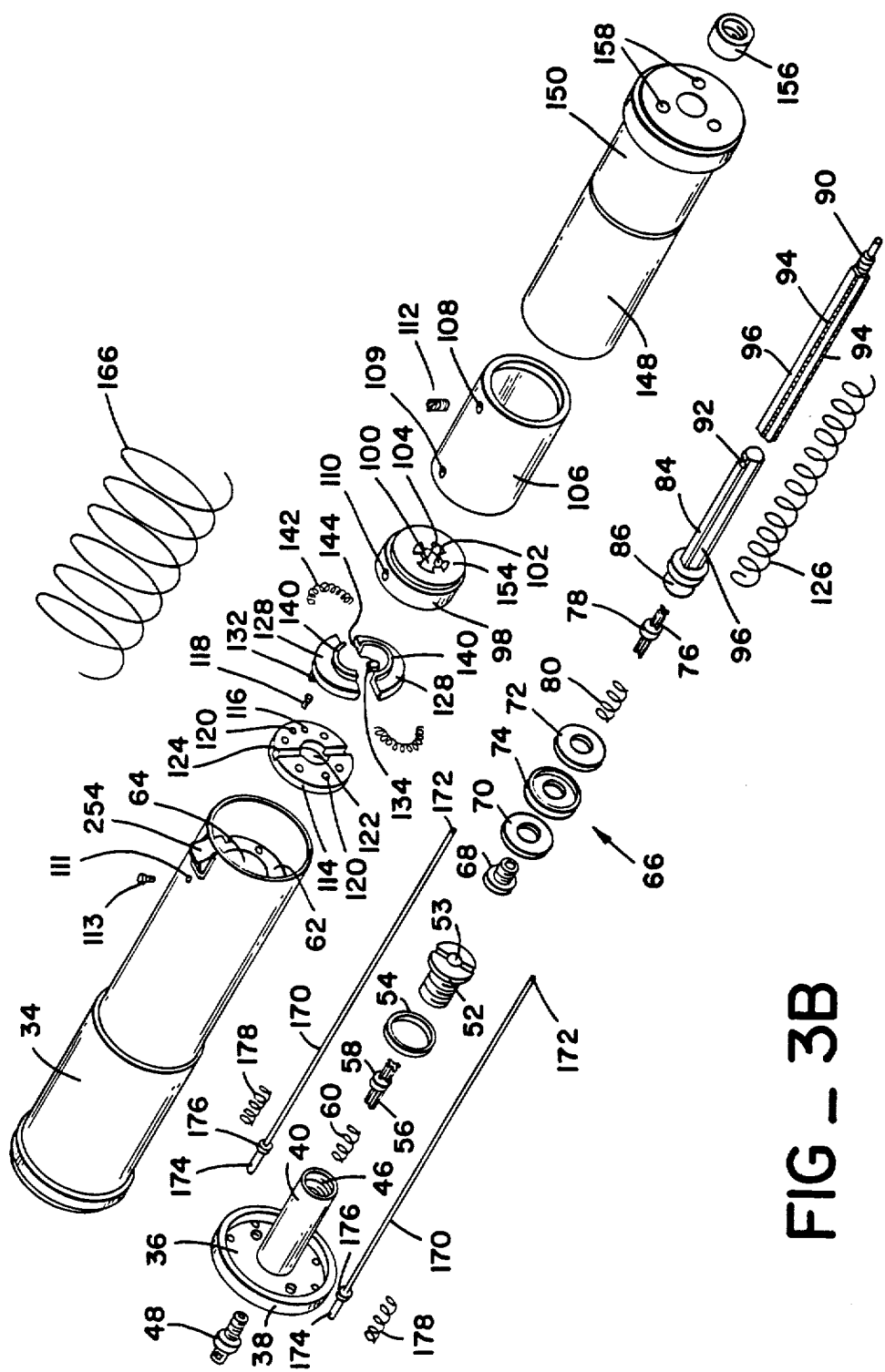
FIG_3B

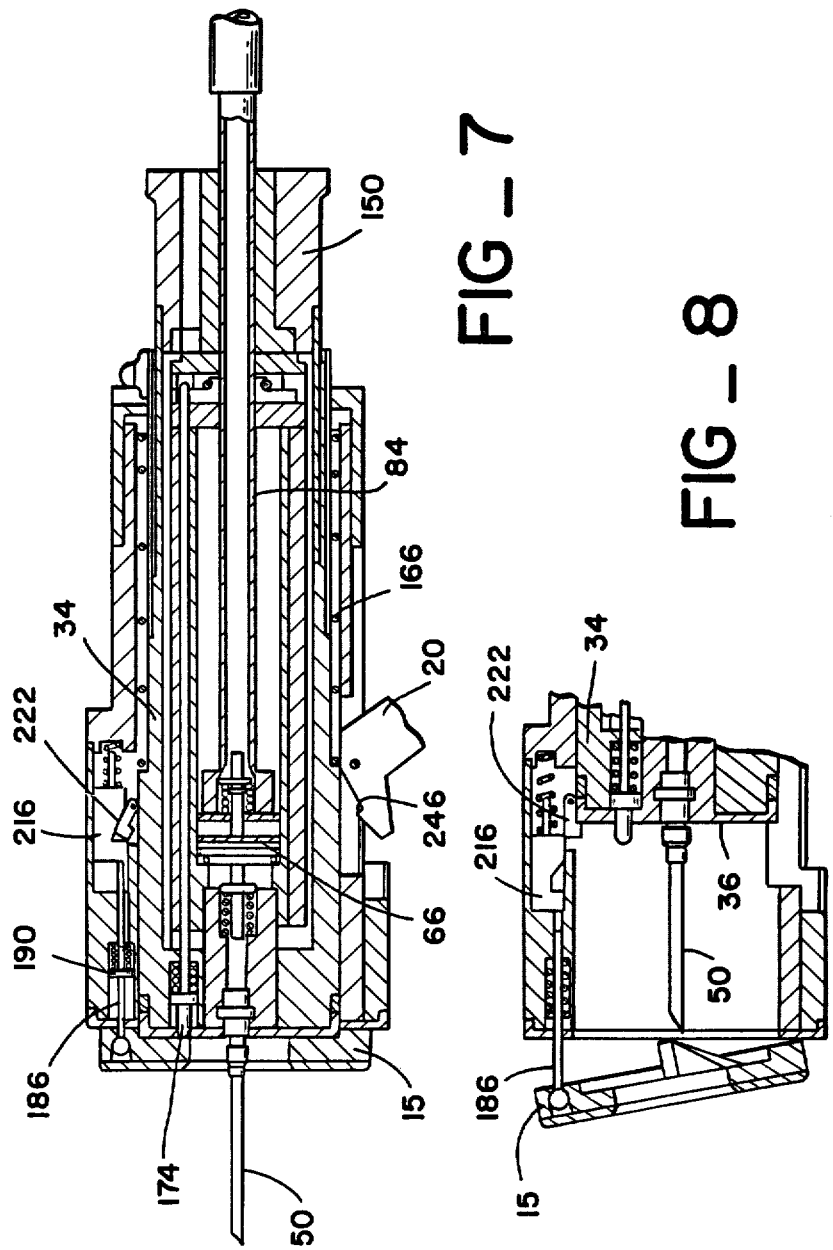

4,487,602

INJECTION DEVICE

This is a continuation of application Ser. No. 301,661, filed Sept. 14, 1981 now U.S. Pat. No. 4,403,989.

BACKGROUND OF THE INVENTION

1. Field of the Invention

The present invention relates to an injection device particularly suitable for the intraruminal injection of medicaments, as fluid solutions or suspensions, to ruminants. More particularly, the invention relates to an injection device having needle actuation means and dose delivery actuation means which substantially eliminate the possibility of administering a dose to a host animal outside of the intended dose delivery area.

2. State of the Art

Numerous automatically actuable injection devices have been described in the prior art, as for example in U.S. Pat. Nos. 3,016,897; 3,051,173; 3,064,650; 3,114,370; 3,141,583; 3,430,626; 3,494,358; 3,677,246; 3,727,614; and 3,809,083. While the prior art devices typically provide for actuation of the injection device when the injection device is brought into contact with the surface of a host to be injected, they are not concerned with the spatial orientation of the surface being injected and the injection device itself, which controls the ultimate site at which delivery of the injection dose will occur. In instances where it is desirable to inject a medicament dose into a particular body cavity of a host or at a particular intramuscular layer within the host, it is of primary importance to control the direction at which the injection device enters the host animal and the spatial orientation of the injection surface and the injection delivery system. An example of such an instance of use is the direct injection of medicaments, e.g. anthelmintics, into the rumen of a ruminant, such as cattle, sheep and the like. For each particular ruminant the general location of the rumen is known and by an appropriately directed injection through the outer skin layer, injections can be made directly into the rumen. However, in order to ensure insertion of the needle into the rumen, the orientation of the injecting instrument with respect to the host animal must be controlled prior to injection. Thus, there is a need to prevent the actuation of the injection mechanism unless the injection delivery system is in a proper orientation with respect to the injection surface of the host animal, and also to prevent delivery of the medicament dose unless the injection apparatus is positioned appropriately within the host.

SUMMARY OF THE INVENTION

The present invention is directed to an injection device for injecting a host at an injection surface thereon comprising a base having a forward end and a rearward end, needle carrying means supported on the base and operable to move a needle from a first, retracted position to a second, extended position relative to the forward end of the base, and needle actuation means operatively coupled to the needle carrying means and responsive to the orientation of the needle carrying means and the injection surface of the host, the needle actuation means being operative to permit movement of the needle carrying means from the first position to the second position only when the needle carrying means and the injection surface of the host are in a preferred orientation relative to each other.

In another aspect, the invention relates to an injection device for injecting a host at an injection surface thereon comprising a base having a forward end and a rearward end, needle carrying means supported by the base and operable to move a needle from a first, retracted position, to a second, extended position relative to the forward end of the base, needle actuation means operatively coupled to the needle carrying means and responsive to the orientation of the needle carrying means and the injection surface of the host, the needle actuation means being operative to permit movement of the needle carrying means from the first position to the second position only when the needle carrying means and the injection surface of the host are in a preferred orientation relative to each other, dose delivery means operatively connected to the needle carrying means and dose delivery actuation means responsive to the relative position of the needle carrying means and the needle actuation means, the dose delivery actuation means being operable to actuate the dose delivery means only when the needle carrying means and the needle actuation means are in a preferred position relative to each other.

DETAILED DESCRIPTION OF THE DRAWINGS

FIG. 1 is a perspective view of the injection device of the present invention;

FIGS. 2, 2A and 2B are side elevational views in cross-section of a top portion of the injection device in its cocked position;

FIGS. 3A and 3B are exploded views of the component parts of the injection device;

FIG. 7 is a cross-sectional view of a top portion of the injection device after release of the dose delivery means; and FIG. 8 is a cross-sectional view of a front portion of the injection device illustrating a non-preferred orientation of the needle carrying means with respect to a host animal which precludes release of the needle actuation means.

DETAILED DESCRIPTION OF THE INVENTION

Figure 6:
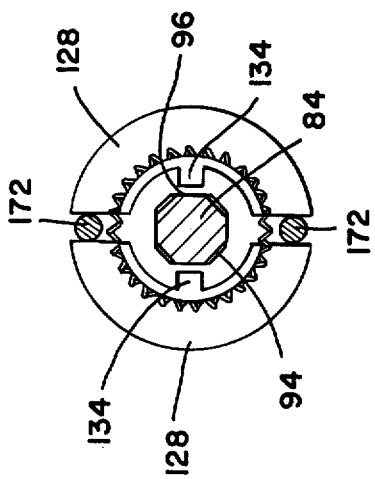
FIG. 6 is a view of the sear retaining mechanism of the dose release means.

With reference to the FIGS. 1 and 2, the injection device 10 of the present invention comprises a base or housing 12 supported on a handle 14. A front end cap 16 is positioned on the end of housing 12 and a brace plate 15, the function of which will be described more fully hereinafter, is positioned forwardly of front-end cap 16. The housing 12 encompasses a needle carrying means 22, dose delivery means 26, dose delivery actuation means 28 and a portion of the needle actuation means 24. A trigger 20 is mounted upon the front surface of handle 14 for actuation by a user. The housing 12 is closed by a rear end cap 18 through which extends cocking means 30 including a cocking grip 150 which can be grasped by the user. In use, brace plate 15 is placed against the surface of a host to be injected and forcibly compressed against front end cap 16 to actuate the needle carrying means such that upon actuation of the trigger by a user the needle carrying means and the needle 50 extend into and through the surface of the host to be injected. After the host has been injected, the injection device 10 is removed from the animal and the cocking means 30 must be actuated by the user to prepare injection device 10 for another dose application.

With particular reference to FIGS. 2A and 2B and FIGS. 3A and 3B, housing 12 is adapted to receive a needle piston 34 which is slideably moveable therein. A needle support plate 36 formed with a flange 38 and a rearwardly extending tubular connector 40 is connected to the forward end of needle piston 34. A bushing 39 is positioned between flange 38 and the forward end of piston 34. Tubular connector 40 is formed with a bore 42 having a threaded front end 44 and a threaded rear end 46. Threaded front end 44 is adapted to receive a needle hub 48 to which a needle 50 can be attached by conventional means (e.g. Luer-Lok or threaded connection). Threaded end 46 of tubular connector 40 is adapted to receive a threaded, front check-valve housing 52 in which is retained a front check valve 56. Check-valve 56 is of a conventional type, having an O-ring 58 and a spring 60 which forces check-valve 56 against the check-valve seat 61 formed in the inner bore 53 of check-valve housing 52.

A cylindrical syringe body 62 is mounted within needle piston 34 and extends substantially the length thereof. Syringe body 62 is provided with a lip 63 on its inner circumfrence adjacent the end near tubular connector 40. The forward end of syringe body 62 fits about the end of tubular connector 40 and is retained thereon by the action of check-valve housing 52. An O-ring 54 is interposed between check-valve housing 52 and lip 63 of syringe body 62 to provide a seal thereon. A chamber 64 is defined by the head of check-valve housing 52 and a piston assembly 66 which is slideably received within the inner bore of syringe body 62. Piston assembly 66 includes a rear check-valve housing 68 and a pair of piston seals 70 and 72 which are positioned on either side of piston body 74. Check-valve housing 68 is threadedly received within piston rod head 86 which is formed at the end of piston rod 84. A rear check-valve 76 is provided within check-valve housing 68 and includes an O-ring 78 and a valve-spring 80 which biases the check-valve toward the rearward end of piston rod 84. A valve seat 82 is provided in piston rod head 86 upon which O-ring 78 is seated to prevent flow through the check-valve in the rearward direction.

Piston rod 84 is provided with a bore 88 extending the length thereof and communicating at its rearward end with a tubing connector 90. Tubing connector 90 is adapted to be connected to a fluid supply tube which can be connected to a bulk source of medicament typically provided as a fluid solution or suspension. Piston rod 84 is additionally provided with a plurality of truncated threads 94 on a substantial portion of the length thereof adjacent its rearward end. The truncated threads 94 are separated by flats 96 which serve to stablize the piston rod during its movement within bushing 98.

Bushing 98 is formed with a central hole 100 having flat surfaces 102 which complement the flats 96 on piston rod 84. Additionally, slots 104 are provided in bushing 98 to accomodate threaded portions 94 of piston rod 84 as piston rod 84 moves forwardly and rearwardly through the bushing. A generally cylindrical retainer 106 is provided to retain bushing 98 on the rearward end of syringe body 62. That retention is accomplished by means of a set screw 112 which passes through hole 108 in retainer 106 and hole 110 in bushing 98. The forward end of retainer 106 is slideably received over the rearward end of syringe body 62 and is fastened thereto by conventional means such as a set screw 113 through holes 109 and 111.

A guide ring 114 is fastened by means of screws 118 through holes 116 to the rearward end of syringe body 62. A central hole 122 is provided in guide ring 114 to accommodate rod 84. Bushing 98 is formed with a step-shaped recess 107 on the forward surface thereof to accommodate a pair of sears 128 which ride upon piston rod 84. Sears 128 are captured between guide ring 114 and bushing 98. A certain amount of movement of sears 128 is however permitted as will be described more fully hereinafter. Sears 128 are provided with a vertically extending rib 132 on the forward face thereof which is adapted to be received and slideably moved within slots 124 provided in guide ring 114. Sears 128 are each additionally provided with a tab 134 which is adapted to be received within slots 92 of piston rod 84. A collar 140 is formed on each of sears 128 on the rearward facing surface thereof to receive a spring 142 which biases sears 128 toward a closed position. Each of sears 128 is provided with a bevelled surface 144 facing toward the forward end of the injection device. Guide ring 114 is also provided with a pair of holes 120, each of which is adapted to receive a dose release rod 170 which extends from the foward edge of flange 38 of needle support plate 36 rearwardly through syringe body 62 to guide ring 114. The function of dose release rods 170 and their interaction with sears 128 and piston rod 84 will be described subsequently.

At the rearward end of piston rod 84 is mounted a calibration ring 148 having a cocking grip 150 attached thereto. The calibration ring 148 and cocking grip 150 are threaded onto truncated threads 94 on rod 84 conveniently by means of a threaded insert 156 which is fastened within cocking grip 150. Alternatively, threads could be formed on the inner bore of cocking grip 150. The forward end of cocking grip 150 is provided with a stop surface 152 which is adapted to contact surface 154 formed on the outer surface of bushing 98 when the dose is delivered to the host animal. The distance between stop surface 152 and stop surface 154 can be varied by threading calibration ring 148 and cocking grip 150 forwardly or rearwardly, as the case may be, on piston rod 84. Calibration ring 148 is adapted to slide within annular space 155 formed between the outer surface of retainer 106 and the inner surface of extension 35 formed at the rearward end of needle piston 34. In order to ensure rapid movement of piston assembly 66 when a dose is being delivered to a host animal, vent holes 158 are provided within cocking grip 150 to vent the space formed between surfaces 152 and 154 and the inner wall of calibration ring 148 when surface 152 is moved toward surface 154.

The needle carrying means of the invention, generally designated 22, comprises a needle piston 34 slideably mounted within housing 12. Needle support plate 38 is attached to the forward end of needle piston 34 and the rearward end of needle piston 34 extends through rear end cap 18. Rear end cap 18 is attached to housing 12 and retains a bushing 164 between the rearward end of housing 12 and a shoulder 162 formed in end cap 18. Needle piston 34 is also formed with a shoulder 160 and a needle spring 166 is retained between bushing 164 and shoulder 160. Needle piston 34 is adapted to move from a first, retracted position at which needle 50 is adjacent to or rearward of front end cap 16 to a second, extended position whereat needle 50 extends forwardly of brace plate 15. At the first, retracted position of needle piston 34, needle spring 166 is compressed and the needle piston 34 is in its cocked or ready to fire position. Upon release of the needle actuation means 24, which will be described more fully subsequently, needle spring 166 expands from its compressed configuration and forces needle piston 34 forwardly in housing 12. At the full extended travel of needle piston 34, assuming that brace plate 15 and front end cap 16 are in a preferred, relative position i.e. immediately adjacent one another, the dose delivery means 26 will be actuated by dose delivery actuation means 28 to deliver a medicament dose to the host animal.

The needle actuation means includes the aforesaid brace plate 15 and means operatively coupling brace plate 15 to the needle carrying means such that the needle carrying means will be permitted to move forwardly from its first, retracted position to its second, extended position only when brace plate 15 and the forward end of housing 12 and end cap 16 are in a preferred orientation, e.g. substantially perpendicular to each other. The means operatively coupling brace plate 15, which is adapted to contact the surface of the host to be injected, is illustrated by three brace plate rods 186 having generally spherical heads 188 and longitudinally extending shaft portions 189. A ring clip 190 is provided intermediate of head 188 and the end of shaft 189 and functions to retain each rod 186 in slot 210 by the action of retainer collar 192. The brace plate rods 186 extend within and through slots 194 positioned generally equidistantly at about 120° about retainer collar 192. Slots 194 correspond positionally to slots 182 in brace plate 15 into which rods 186 extend. A ring extension 193 is provided on the forward face of retainer collar 192 to act as a stop means to prevent needle piston 34 from being driven out from the forward end of the insertion device. The spherical head 188 of each of rods 186 is received within a substantially spherical chamber 184 within brace plate 15. A cover 198 is secured over the forward end of brace plate 15 by means of screws 202 extending through holes 200.

An enlarged bore or slot 212 is formed in the forward end of slot 210 in housing 12. Slot 212 accomodates a spring 204 extending between ring clip 190 and the shoulder formed by the junction of slots 210 and 212. Spring 204 biases each of the brace plate rods 186 toward the forward end of the insertion device. At the end of each of the slots 210 is provided a recess 214 which receives a cam 216 and a sear 222. Cam 216 has a tang 218 extending from the rearward end thereof and a notch 232 formed in the bottom surface thereof. Cam 216 is adapted to slide forwardly and rearwardly within slot or recess 214. A spring 220 is positioned about tang 218 and biases cam 216 toward the forward end of the insertion instrument instrument. Sear 222 is formed of a generally U-shaped, cross-sectional configuration, having side walls and a bottom wall. Sear 222 is pivotably connected to housing 12 by means of a pin 228 which passes hole 226 in housing 12 and hole 224 in sear 222 to retain sear 222 on housing 12. Additional pins 230 and 234 are included within sear 222 to cooperate with cam 216 and the front end of needle support plate 36, respectively, to capture and release needle piston 34 under appropriate conditions.

Figure 4:
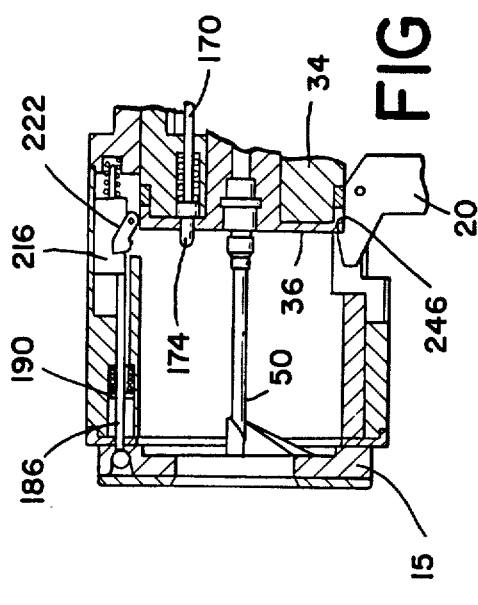
FIG. 4 is a cross-sectional view of a front portion of the injection device illustrating the release of the needle actuation means prior to release of the needle carrying means.

As can best be seen from FIG. 2A, pin 234 in sear 222 contacts the forward surface of needle piston 34 as provided by flange 38 on needle support plate 36. Only one of the sears is shown in its operative position but it is understood that the structure and function of the additional two sears positioned correspondingly with the additional two brace plate rods 186 is the same as the sear described. When the needle actuation means 24 is in its deactivated position, cam 216 is positioned near the forward end of recess 214 under the urging of spring 20. At that position the bottom surface of cam 216 is immediately above pin 230 and sear 222 and prevents sear 222 from pivoting about its pivot pin 228 which would release needle piston 34 for forward movement under the urging of spring 166. However, as shown in FIG. 4, when the brace plate 15 is pressed against an injection surface of a host animal, the housing 12 and the forward surface of end cap 192 are moved forwardly toward brace plate 15 with the effect that brace plate rods 186 slide rearwardly within slots 210 and contact cam 216 thereby urging cam 216 toward the rearward end of housing 12. As cam 216 is urged rearwardly, notch 232 in cam 216 moves to a position over pin 230. At that position, sear 222 begins to pivot about pivot pin 228 and rides upwardly on the forward surface of notch 232. That motion releases pin 234 from the front surface of needle support plate 36. It should be pointed out, however, that although sear 222 may have released its contact with the front surface of needle support plate 36, an additional retainer for the needle carrying means is provided by lip 246 on trigger 20 which retains needle carrying means 22 in position for firing until trigger 20 is actuated.

A particularly advantageous aspect of the present invention precludes release of the needle carrying means 22 unless and only when brace plate 15, which is contacting the injection surface of the host animal, is perpendicularly oriented with respect to the needle carrying means 22 and the housing 12 in which it is contained. When the preferred orientation which is desired between the needle actuation means 24 and the needle carrying means 22 is perpendicularity, brace plate rods 186 are each formed of equal lengths. Thus, although two of the brace plate rods may be fully extended rearwardly so as to actuate two of cams 216 and sears 222, if the brace plate 15 is skewed out of a plane of perpendicularity, as shown in FIG. 8, one of the brace plate rods 186 will not be fully extended rearwardly so as to force cam 216 into a position whereat pin 230 can rise within notch 232. Accordingly, even if two of sears 222 are released from the forward end of needle support plate 36, one of the sears 222 will still remain in its engaged position. That sear 222 then will resist forward movement of needle piston 34. When brace plate 15 is in the preferred orientation of being perpendicular to end cap 192 and housing 12 and needle carrying means 22, each of the sears 222 is released from the forward end of needle support plate 36 and the only remaining restraint on the movement of needle piston 34 is provided by lip 246 on trigger 20. The needle carrying means 22 can then be released by actuation of trigger 20 by an operator to remove lip 246 from the front surface of needle support plate 36 thereby releasing the same and allowing needle piston 34 to be urged by spring 166 forwardly within housing 12 to extend needle 50 through brace plate 15 and into and through the injection surface of the host animal to be injected as shown in FIG. 5.

The trigger mechanism employed in the injection device can be seen most clearly from FIG. 3A. A trigger pin 236 passes through a hole 237 in trigger 20 and is connected at each end to housing 12 in a manner such that trigger 20 pivots about trigger pin 236. A recess 240 is formed in trigger 20 to receive a trigger spring 238. A trigger guide 242 is provided to ride in slot 244 on handle 14. Guide 242 and slot 244 provide a cooperative mechanism for controlled movement of trigger 20 about trigger pin 236. Trigger spring 238 serves to return trigger 20 to its cocked position whereat lip 246 of trigger 20 contacts the front face of needle support plate 36 to prevent forward movement of needle piston 34.

Figure 5:
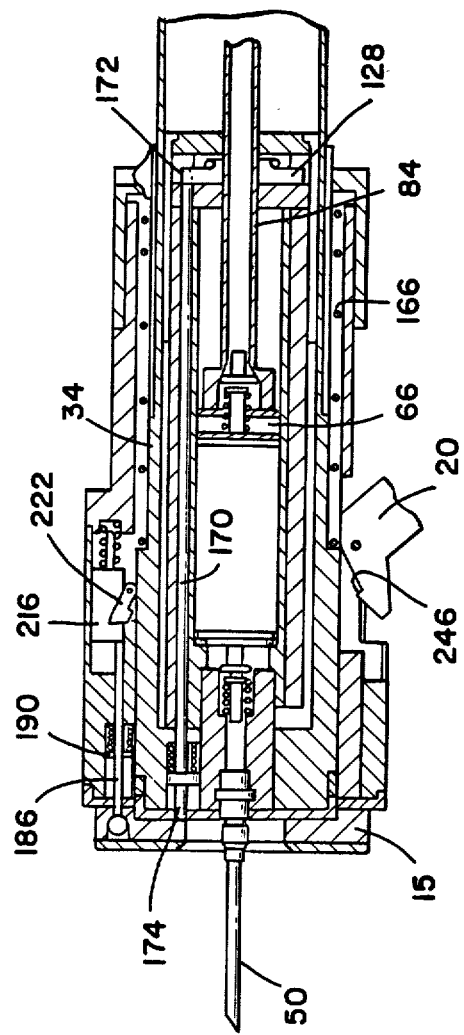
FIG. 5 is a cross-sectional view of a front portion of the injection device with the needle carrying means having been released and the dose release means illustrated just prior to release of a medicament dose.

With particular reference to FIGS. 5, 6 and 7, when the needle carrying means 22 is propelled forwardly under the action of spring 166 to a forward position, the heads 174 of dose release rods 170 contact the inner surface of brace plate 15 and dose release rods 170 are forced rearwardly against the urging of springs 178 such that the rearward ends 172 of dose release rods 170 contact the bevelled surfaces 144 of sears 128 located within the recess 107 formed in bushing 98. As the rearward ends 172 of dose release rods 170 pass between the bevelled surfaces 144 of sears 128 as shown in FIG. 6, the sears 128 are urged apart from each other against the action of spring 142 such that tabs 134 are drawn out from engagement with notches 92 in piston rod 84. In that configuration, piston rod 84 is free to move forwardly under the urging of spring 126 and forces piston assembly 66 forwardly within syringe body 62 to express the fluid medicament dose contained within chamber 64 as shown in FIG. 7. Front checkvalve 56 is a one-way valve which is operable to permit flow of the medicament dose toward the forward end of housing 12 and through bore 42 and needle 50 into the host animal being injected and prevent flow in the opposite direction.

After the injection has been completed and the injection device 10 and brace plate 15 are removed from contact with the injection surface of the host animal, springs 204 operate to urge brace plate rods 186 forwardly within slots 210 and extend brace plate 15 from the front surface of retainer collar 192. The injection device then is ready to be cocked by an operator for a subsequent injection. Cocking of the injection device is accomplished by the operator gripping and pulling rearwardly on cocking grip 150, which is attached to piston rod 84, to draw piston rod 84 rearwardly out from housing 12. As piston rod 84 is drawn rearwardly, flats 96 slide upon flat surfaces 102 formed in bushing 98. That rearward movement continues until slots 92 in piston rod 84 are opposite tabs 134 of sears 128, at which time under the urging of spring 142 sears 128 are compressed and tabs 134 become engaged with notches 92. The movement of piston rod 84 and piston assembly 66 creates a partial vacuum within chamber 64 of syringe body 62, which draws fluid through the inner bore 88 of piston rod 84 from the medicament source and through one-way check-valve 76 into chamber 64.

During the movement of piston rod 84 in the rearward direction, ends 172 of dose release rods 170 are removed from sears 128 thus permitting the engagement of tabs 134 with notches 92. Additional rearward movement of cocking grip 150 operates to slide needle piston 34 within housing 12 rearwardly, compressing spring 166 such that needle piston 34 reaches a position at which pins 234 in sears 222 can again engage the front surface of needle piston 34 on needle support plate 36. During rearward movement of needle piston 34, springs 220 extending over tangs 218 on cams 216 force cams 216 forwardly within slots or recesses 214 thereby pressing downwardly on pins 230 at the upper surface of sears 222 and causing sears 222 to pivot downwardly about pivot pins 228. Additionally, trigger spring 238 urges trigger 20 forwardly to pivot about trigger pin 236 such that lip 246 formed on the upper surface of trigger 20 can again engage needle piston 34 at the front surface of needle support plate 36. After the injection device 10 has been fully cocked in the manner described, the injection device 10 is ready for a subsequent injection of a host animal.

While the preferred orientation for intraruminal injections is that the needle carrying means 22 and the needle actuation means 24 be perpendicular to the injection surface of the host animal, it is apparent that other orientations could be used as well depending on the particular application of the injection device 10. For example, if it is desired that the needle 50 be injected at an angle through the injection surface of the host animal when the brace plate 15 is pressed flat against that surface, one need only adjust the lengths of brace plate rods 186 such that sears 222 are released only when the needle carrying means 22 is in its preferred angular orientation with respect to the injection surface. Release of sears 222 on the surface of needle support 36 when the needle carrying means 22 is at an angular orientation to the injection surface, permits actuation of the needle carrying means including needle piston 34 by trigger 20 when injection is desired.

The amount of medicament dose administered to the host animal is controlled by the distance between stop surfaces 152 and 154 as described previously. The extent of movement of piston rod 84 and piston assembly 66 upon actuation of the dose release means, depends on the distance between surfaces 152 and 154, and there is a direct linear correspondence between the length of travel of piston 66 within chamber 64 and the medicament dose supplied. By threading grip 150 forwardly upon piston rod 84 the distance between stop surfaces 152 and 154 is decreased and correspondingly decreases the amount of dose administered to the host animal. Threading of the grip 150 rearwardly on piston rod 84 increases the distance between stop surfaces 152 and 154 and increases the amount of dose administered to the host animal. Calibration markings can be appropriately placed upon calibration ring 148 to indicate the dose being administered.

Alternative means for moving grip 150 forwardly and rearwardly along piston rod 84 can be provided. For example, grip 150 may be made slidable upon piston rod 84 by replacing the truncated threads on piston rod 84 with a single track which can be engaged at various positions by a releasable, locking pin placed on grip 150.

In order to ensure proper delivery of a medicament dose to the host animal, it may be necessary to prime the injection device prior to use. Priming of the device typically will be necessary when the injection device has been disconnected from its medicament source, thus permitting air to enter the fluid transfer line from the medicament source, or when a fresh medicament source is connected to the injection device. To that end, a pair of arcuate ramps 250 are formed on the inner surface of brace place 15 as shown most clearly in FIG. 2A and 3A. Ramps 250 merge with brace plate 15 at ends 251 thereof and terminate in a land area 252 at the other end thereof. Ramps 250 are oriented with respect to heads 174 of dose release rods 170 such that in the normal injection mode for the injection device, ends 251 of ramps 250 are substantially opposite heads 174. Upon turning of needle piston 34 approximately 90° counterclockwise, land areas 252 are opposite heads 174.

To faciliate priming of the injection device, a catch 254 is formed on the outer surface of needle piston 34 at the rearward end thereof and is pivotably attached thereto, conveniently by means of a living hinge or the like. When catch 254 is depressed and needle piston 34 is moved forwardly in housing 12, catch 254 passes through a first notch 256 formed in rear end cap 18. As needle piston 34 is moved forwardly, a tab extension 260 formed on the outer surface of needle piston 34 near its forward end (as shown by dashed lines in FIG. 2A) slides within a longitudinal groove or slot 262 formed by ribs 264 on the inner surface of housing 12. Circumferentially extending ribs 266 form an arcuate slot or groove 268 on the inner surface of housing 12. Groove 268 is adapted to receive tab extension 260 upon counterclockwise rotation of needle piston 34.

When needle piston 34 has been moved forwardly within housing 12 and is rotated approximately 90° counterclockwise, catch 254 locates within notch 258 and tab extension 260 is rotated upwardly into groove 268. Tab extension 260 is captured between ribs 266 to prevent axial movement of needle piston 34 during the priming operation. Counterclockwise rotation of needle piston 34 also causes head 174 of dose release rods 170 to ride upwardly on ramps 250 such that heads 174 are located upon land areas 252 when needle piston 34 has been rotated 90° counterclockwise. That movement forces dose release rods 170 rearwardly to release sears 128 from engagement with piston rod 84.

Since sears 128 are released in the aforesaid configuration, piston rod 84 can be reciprocated freely to expel air from the fluid system through syringe body 62 and chamber 64 outwardly from needle 50. Each reciprocation of piston rod 84 draws medicament from the source through the rearward end of the injection device and expels air from the forward end of the injection device until chamber 64 is filled with fluid medicament.

When injection device 10 has been primed, needle piston 34 is rotated approximately 90° clockwise to move land area 252 out of engagement with heads 174 of dose release rods 170. At the same time, tab extension 260 is released from groove 268. Springs 178 then force dose release rods 170 forwardly until sears 128 are released and engage notches 92 in piston rod 84, when the injection device has been cocked in the manner described previously.

While this invention has been described with reference to the specific embodiments thereof, it should be understood by those skilled in this art that various changes can be made and equivalents may be substituted without departing from the true spirit and scope of the invention. All such modifications are intended to be within the scope of the claims appended hereto.

What is claimed is:

1. A hand-held injection device for injecting a host animal at an injection surface thereon comprising:
    a base having a forward end and rearward end;
    needle-support means on said base adapted to support a needle for injection into the host animal;
    a contract surface associated with the base and positioned remotely from the forward end of the base, the contact surface being adapted to contact the injection surface of the host animal to provide a means to orient the base and needle-support means with respect to the injection surface, said contact surface having a perimeter circumscribing the needle and sufficiently large to permit and facilitate orientation of the needle-support means and the injection surface of the host animal, and said contact-surface having an opening therein and being moveable relative to the needle-support means to permit a needle supported thereon to be moved through said opening into the injection surface upon urging of the base toward the injection surface; and
    dose delivery means to automatically dispense a medicament dose into the host animal when said contact surface and the forward end of said base are in a preferred position relative to each other.

2. The injection device of claim 1 wherein said contact surface is annular and the needle extends through said opening of said contact surface when the needle is in a position suitable for injection into the host animal.

3. The injection device of claim 1 including means to limit application of the medicament dose to the host animal unless the needle extends forward from said contact surface.

* * * * *

UNITED STATES PATENT AND TRADEMARK OFFICE
CERTIFICATE OF CORRECTION

PATENT NO. : 4,487,602

DATED : December 11, 1984

INVENTOR(S) : Terrence B. Christensen et al.

It is certified that error appears in the above-identified patent and that said Letters Patent is hereby corrected as shown below:

The term of this patent subsequent to September 13, 2000, has been disclaimed.

Signed and Sealed this

Tenth Day of September 1985

[SEAL]

Attest:

DONALD J. QUIGG

Attesting Officer     Acting Commissioner of Patents and Trademarks - Designate